US012588843B2

(12) United States Patent
Garai et al.

(10) Patent No.: US 12,588,843 B2
(45) Date of Patent: Mar. 31, 2026

(54) SENSOR WITH SUBSTRATE INCLUDING INTEGRATED ELECTRICAL AND CHEMICAL COMPONENTS AND METHODS FOR FABRICATING THE SAME

(71) Applicant: MEDTRONIC MINIMED, INC., Northridge, CA (US)

(72) Inventors: Ellis Garai, Studio City, CA (US); Akhil Srinivasan, Pacific Palisades, CA (US); David C. Antonio, Montrose, CA (US)

(73) Assignee: MEDTRONIC MINIMED, INC., Northridge (CA)

(*) Notice: Subject to any disclaimer, the term of this patent is extended or adjusted under 35 U.S.C. 154(b) by 1021 days.

(21) Appl. No.: 16/391,206

(22) Filed: Apr. 22, 2019

(65) Prior Publication Data

US 2020/0330007 A1 Oct. 22, 2020

(51) Int. Cl.

| | |
|---|---|
| ***A61B 5/1477*** | (2006.01) |
| ***A61B 5/145*** | (2006.01) |
| ***G01N 33/49*** | (2006.01) |
| ***H01L 21/48*** | (2006.01) |
| ***H01L 23/13*** | (2006.01) |
| ***H01L 23/31*** | (2006.01) |
| ***H01L 23/498*** | (2006.01) |
| ***H01L 23/66*** | (2006.01) |

(52) U.S. Cl.

CPC ........ *A61B 5/1477* (2013.01); *A61B 5/14546* (2013.01); *G01N 33/49* (2013.01); *H01L 21/4846* (2013.01); *H01L 23/13* (2013.01); *H01L 23/3157* (2013.01); *H01L 23/49838* (2013.01); *H01L 23/4985* (2013.01); *H01L 23/66* (2013.01); *A61B 2562/125* (2013.01); *H01L 2223/6677* (2013.01)

(58) Field of Classification Search

CPC .............. A61B 5/1477; A61B 5/14546; A61B 2562/125; G01N 33/49; H01L 21/4846; H01L 23/13; H01L 23/3157; H01L 23/49838; H01L 23/4985; H01L 23/66; H01L 2223/6677

See application file for complete search history.

(56) References Cited

U.S. PATENT DOCUMENTS

| | | | |
|---|---|---|---|
| 4,755,173 | A | 7/1988 | Konopka et al. |
| 5,391,250 | A | 2/1995 | Cheney, II et al. |
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |

(Continued)

FOREIGN PATENT DOCUMENTS

CN 113367671 A * 9/2021 ........... A61B 5/0004

*Primary Examiner* — Alex M Valvis
*Assistant Examiner* — Grace L Rozanski
(74) *Attorney, Agent, or Firm* — Foley & Lardner LLP

(57) ABSTRACT

Analyte sensor devices and methods for fabricating analyte sensor devices are presented here. In accordance with certain embodiments, a device for detecting and/or measuring one or more analytes in fluid includes a substrate and one or more analyte sensors disposed on and/or in the substrate. Further, the device includes an integrated circuit disposed on and/or in the substrate. The integrated circuit is electrically integrated with the analyte sensors.

29 Claims, 13 Drawing Sheets

(56) References Cited

U.S. PATENT DOCUMENTS

| | | | |
|---|---|---|---|
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 10,442,679 | B2 * | 10/2019 | Boutaud ............... G01L 9/0042 |
| 10,561,405 | B2 * | 2/2020 | Pizer ...................... B23K 26/38 |
| 2007/0123819 | A1 | 5/2007 | Mernoe et al. |
| 2010/0160861 | A1 | 6/2010 | Causey, III et al. |
| 2013/0041235 | A1 * | 2/2013 | Rogers ................. H05K 1/0283 600/386 |
| 2013/0131468 | A1 * | 5/2013 | Deck .................. A61B 5/14503 604/503 |
| 2014/0005492 | A1 * | 1/2014 | Harttig ............... A61B 5/14735 156/60 |
| 2014/0178909 | A1 * | 6/2014 | Tonks ...................... C12Q 1/32 435/14 |
| 2017/0027514 | A1 * | 2/2017 | Biederman .......... A61B 5/1451 |
| 2017/0100056 | A1 * | 4/2017 | Zhu ......................... H02J 50/10 |
| 2018/0116572 | A1 * | 5/2018 | Simpson ............ A61B 5/14503 |
| 2018/0199873 | A1 * | 7/2018 | Wang ..................... C12Q 1/006 |
| 2019/0090743 | A1 * | 3/2019 | Hahn .................... H01L 21/486 |
| 2019/0117133 | A1 * | 4/2019 | Halac ................. A61B 5/14517 |
| 2019/0298232 | A1 * | 10/2019 | Ko ....................... A61B 5/6847 |
| 2019/0336055 | A1 * | 11/2019 | Shah .................... A61B 5/0015 |
| 2021/0060252 | A1 * | 3/2021 | Liu ..................... A61M 5/2033 |
| 2021/0145352 | A1 * | 5/2021 | Rogers .................... B29C 69/00 |
| 2021/0307657 | A1 * | 10/2021 | Halac ................... H05K 999/99 |
| 2021/0345914 | A1 * | 11/2021 | Moein .................. A61B 5/6848 |

* cited by examiner

SENSOR WITH SUBSTRATE INCLUDING INTEGRATED ELECTRICAL AND CHEMICAL COMPONENTS AND METHODS FOR FABRICATING THE SAME

TECHNICAL FIELD

Embodiments of the subject matter described herein relate generally to sensors for monitoring analyte levels in patients. More particularly, embodiments of the subject matter relate to glucose sensors, to and to methods for fabricating glucose sensors.

BACKGROUND

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and can deliver insulin into a body via an infusion tube with a percutaneous needle or a cannula placed in subcutaneous tissue.

As of 1995, less than 5% of Type 1 diabetic individuals in the United States were using infusion pump therapy. Currently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, and are increasingly prescribing continuous infusion for patients.

An infusion pump system may include an infusion pump that is automatically and/or semi-automatically controlled to infuse insulin into a patient. The infusion of insulin may be controlled to occur at times and in amounts that are based, for example, on blood glucose measurements obtained from an embedded analyte sensor, such as a glucose sensor, in real-time.

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

Equation 1

$$\text{GLUCOSE} + O_2 \xrightarrow{\text{GLUCOSE OXIDASE}} \text{GLUCONIC ACID} + H_2O_2$$

Equation 2

$$H_2O_2 \longrightarrow O_2 + 2\,H^+ + 2\,e^-$$

In equation 1, the glucose oxidase is used to catalyze the reaction between glucose and oxygen to yield gluconic acid and hydrogen peroxide ($H_2O_2$). The hydrogen peroxide reacts electrochemically as shown in equation 2 and the resulting current can be measured by a potentiostat. These reactions, which occur in a variety of oxidoreductases known in the art, are used in a number of sensor designs.

Typically, a glucose sensor will be coupled to a circuit board system coupled to at least a microcontroller, a radio, and an application-specific integrated circuit. With the continued scaling of semiconductor components, it is apparent that the circuit board components will be integrated onto a single chip in a system on a chip (SOC) arrangement. With this advance, the number of layers and traces of the circuit board will be reduced. However, because the glucose sensor is a separate chemical component, processing will still require a time-consuming and complex mechanical connection process for mounting the glucose sensor to the circuit board components. Also, the mechanical interface between the chemical and electronic components will remain as a potential point of failure. Further, device level testing of the sensor device cannot be performed until the sensor is mounted to the circuit board, which complicates factory calibration processing and high manufacturing throughput.

Accordingly, it is desirable to have an improved analyte sensor, and improved methods for fabricating analyte sensors that address the shortcomings of traditional sensor systems and methods. Furthermore, other desirable features and characteristics will become apparent from the subsequent detailed description and the appended claims, taken in conjunction with the accompanying drawings and the foregoing technical field and background.

BRIEF SUMMARY

Analyte sensor devices and methods for fabricating analyte sensor devices are presented here. In accordance with certain embodiments, a device for detecting and/or measuring one or more analytes in fluid includes a substrate and one or more analyte sensors disposed on and/or in the substrate. Further, the device includes an integrated circuit disposed on and/or in the substrate. The integrated circuit is electrically integrated with the analyte sensors.

A method for fabricating an analyte sensor device is also presented here. The method includes forming conductive circuitry on and/or in a substrate. The method further includes forming an integrated circuit device on and/or in the substrate, wherein the integrated circuit device is selectively electrically connected to the conductive circuitry. Also, the method includes depositing chemistry layers on and/or in the substrate to form at least one analyte sensor integrated into the conductive circuitry In another embodiment, a method for fabricating analyte sensor devices is provided. The method includes providing a sheet of a substrate and forming conductive circuitry on and/or in the substrate in selected locations. Further, the method includes forming an integrated circuit device on and/or in the substrate in each location, wherein each integrated circuit device is selectively electrically connected to respective circuitry therein. Also, the method includes depositing electrochemical sensing layers on and/or in the substrate to form an analyte sensor in each location integrated with the respective circuitry therein. The method further includes cutting the sheet to separate each analyte sensor device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
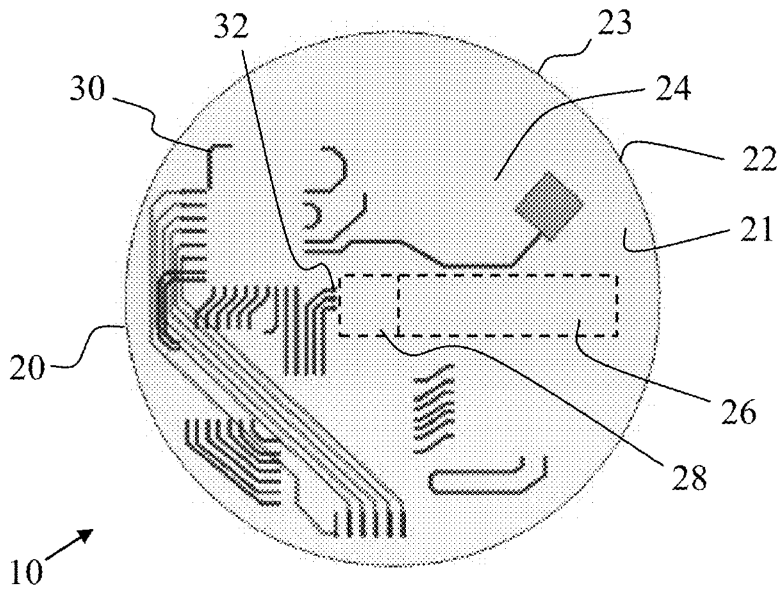
FIG. 1 is a plan view of a top surface of a partially fabricated analyte sensor device after formation of electrical circuitry in accordance with an embodiment.

The following detailed description is merely illustrative in nature and is not intended to limit the embodiments of the subject matter or the application and uses of such embodiments. As used herein, the word “exemplary” means “serving as an example, instance, or illustration.” Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Also, while the preceding background discusses glucose sensing and exemplary analyte sensors may be described as glucose sensors herein, such description is for convenience and is not limiting. The claimed subject matter may include any type of analyte sensor utilizing an embodiment of the integrated electronic and chemical components described herein. Further, embodiments may provide for simultaneously detecting glucose, oxygen, lactic acid, and/or other analytes.

In an exemplary embodiment, an analyte sensor device includes a chemical component and an electrical component. The chemical component, such as an analyte sensor including various electrochemical sensing layers for detecting and/or measuring one or more analytes in a fluid, is formed on a same substrate as an electrical component, such as an integrated circuit device or devices. Conductive traces are formed in and/or on the substrate to selectively electrically integrate the chemical component and the electrical component. For example, electrical circuitry of the integrated circuit may be connected directly to electrodes of the sensor via conductive traces that are electroplated or otherwise formed on and/or in the substrate. As a result, the sensor is electrically integrated with the electrical circuitry and no additional mechanical connections are necessary to couple the sensor and the integrated circuit. Therefore, fabrication of the analyte sensor device avoids complex assembly processes in which fabricated analyte sensors are mounted to and contacted with fabricated integrated circuit devices.

As used herein, “over” is used without reference to the orientation of the device shown in the Figures, such that an element that is over the top surface is farther from the bottom surface than the top surface is, and an element that is over the bottom surface is farther from the top surface than the bottom surface is.

In certain embodiments, electrical components of the integrated circuit are formed over and/or in a top surface of the substrate while chemical components of the sensor are formed over and/or in a bottom surface of the substrate.

In certain embodiments, at least a portion of the electrical components of the integrated circuit are formed over the top surface and at least a portion of the chemical components of the sensor are formed over the bottom surface.

In certain embodiments, electrical components of the integrated circuit are formed over and/or in the top surface of the substrate while chemical components of the sensor are formed over and/or in the bottom surface of the substrate and over and/or in the top surface of the substrate.

In certain embodiments, electrical components of the integrated circuit are formed over and/or in the top surface of the substrate while a first sensor electrode is disposed on the top surface and a second sensor electrode is disposed on the bottom surface.

In exemplary embodiments, certain electrical components of the sensor, such as working electrodes, are formed over and/or in the bottom surface of the substrate. Other electrical components of the sensor, such as counter and reference electrodes, may be formed over and/or in the bottom surface of the substrate or over and/or in the top surface of the substrate.

Further, in exemplary embodiments, the analyte sensor is configured for pivotable movement with respect to the rest of the substrate such that the sensor may be positioned at a selected angle to the rest of the substrate, such as perpendicular to the rest of the substrate. In certain embodiments, a voided region may be formed in the substrate to partially surround a prong on which the analyte sensor is formed to provide for such movement. Also, in certain embodiments, the device may include two prongs partially separated from the rest of the substrate to allow for pivotable movement, with each prong having a sensor thereon. In such embodiments, the prongs may be formed opposite one another such that, after pivoting each prong perpendicular to the rest of the substrate, the bottom surface of the prongs face opposite directions.

Also, while in certain embodiments, the entire device is formed by a flexible substrate, in other embodiments, the device includes a rigid substrate portion and rigid conductive layers.

According to certain embodiments, examples of devices including analyte sensors as described herein may be implemented in a hospital environment to monitor levels of glucose in a patient. Alternatively, according to certain embodiments, examples of devices including analyte sensors as described herein may be implemented in non-hospital environments to monitor levels of glucose in a patient. Here, a patient or other non-medical professional may be responsible for interacting with analyte sensors.

FIGS. 1-9 illustrate exemplary embodiments of a method for fabricating an analyte sensor device 10. FIG. 1 is a top plan view of the partially fabricated device 10. In FIG. 1, a substrate 20 having a top surface 21 (facing the viewer), and an opposite bottom surface 22. As alluded to above, the orientation of the substrate 20 is not vital and the substrate 20 may be flipped such that the bottom surface 22 faces up and the top surface 21 faces down. In certain embodiments, the substrate 20 is a flexible, electrically insulating material such as a polyimide layer or layers, or other suitable materials. In FIG. 1, the substrate 20 is illustrated as being disk-shaped and having a peripheral edge 23 that is circular; however, the substrate 20 may be provided in any suitable shape.

As shown in FIG. 1, the method includes forming electrical circuitry 30 on and/or in the substrate 20, such as on and/or in the top surface 21 of the substrate 20. For example, the circuitry 30 may include conductive traces, contact pads, conductive filled vias, metallization layers, and the like as are typically formed during integrated circuit fabrication. In certain embodiments, the electrical circuitry 30 is defined by etching a disposed conductive layer into a desired pattern of conductive paths. In exemplary embodiments, the circuitry 30 terminates at terminals 32. In an exemplary embodiment, the terminals 32 extend through the substrate 20 from the top surface 21 to the bottom surface 22. As shown, the circuitry 30 is formed in an integrated circuit region 24 of the substrate 20, i.e., a region where an integrated circuit is to be formed. Also identified in FIG. 1 are a sensor region 26, where a sensor is to be formed, and an interconnecting region 28.

Figure 2:
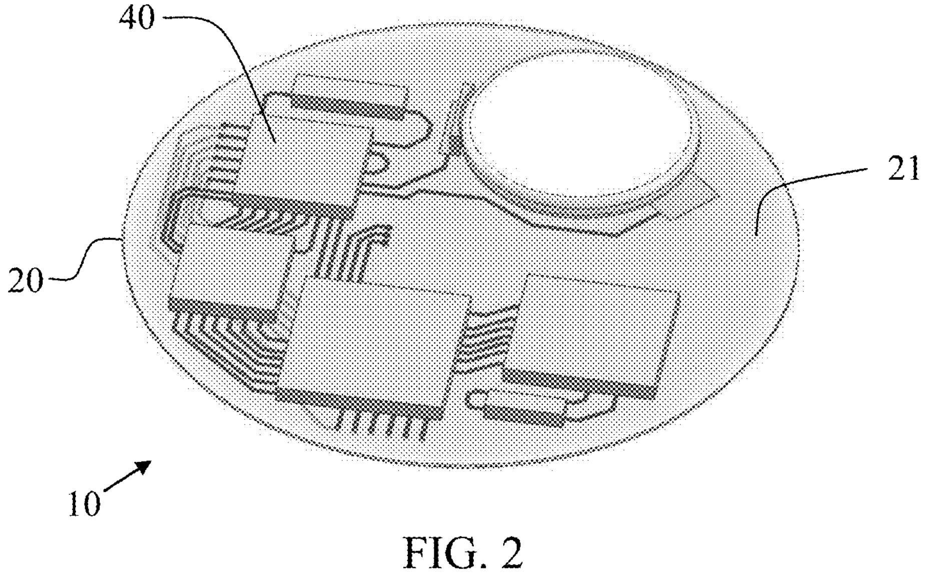
FIG. 2 is a perspective view of the device of FIG. 1 after formation of integrated circuit devices in accordance with an embodiment.

Referring to FIG. 2, a perspective view of the top surface 21 of the substrate 20 of the partially fabricated device 10, the method may continue with the formation of integrated circuit devices 40 over and/or in the substrate 20, such as over and/or in the top surface 21. In certain embodiments, the integrated circuit devices 40 may include a microcontroller, a radio, an analog front end, a battery, and other desired electronic components. Although not illustrated, the devices 40 may be integrated into a single integrated circuit device.

Figure 3:
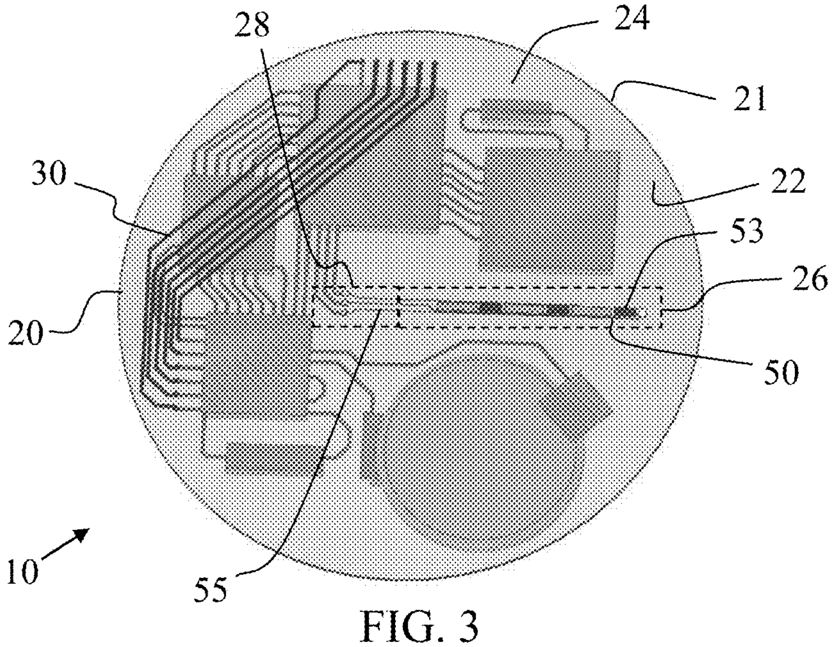
FIG. 3 is a plan view of the bottom surface of the device of FIG. 2, after formation of an analyte sensor thereon in accordance with an embodiment.

FIG. 3 provides a plan view of the bottom surface 22 of the substrate 20. As shown in FIG. 2, the fabrication method continues with the formation of an analyte sensor 50 on and/or over the substrate 20 such as on and/or over the bottom surface 22 of the substrate 20. While illustrated as being on and/or over the bottom surface 22, in other embodiments, the analyte sensor 50 may be formed on and/or over the top surface 21 or on and/or over both the top surface 21 and the bottom surface 22. Further, as single elements in the drawings may be indicative of a plurality of elements, the fabrication method may form at least one analyte sensor 50 on and/or over the top surface 21 and at least one analyte sensor 50 on and/or over the bottom surface 22. As shown in FIG. 3, the analyte sensor 50 is formed in the sensor region 26. The analyte sensor 50 may include electrodes 53, such as working, reference, and counter electrodes.

Figure 4:
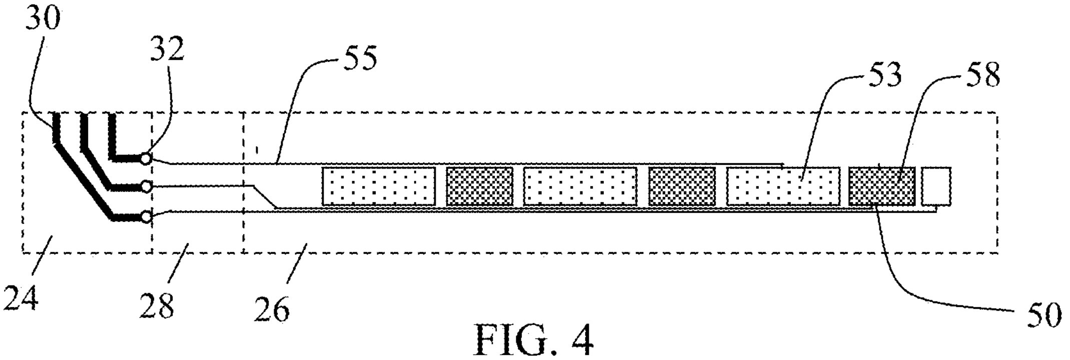
FIG. 4 is a schematic plan view of the sensor region and interconnecting region of FIG. 3 in accordance with an embodiment.

FIG. 4 is an expanded schematic view of the sensor region 26, the interconnecting region 28, and a portion of the integrated circuit region 24 of the device 10 of FIG. 3. As shown, the method further includes forming conductive traces 55 in contact with the terminals 32 of the circuitry 30 in the integrated circuit region 24. The conductive traces 55 extend from the terminals 32, through the interconnecting region 28, and through the sensor region 26 into selective connection with various electrodes 53 of the analyte sensor 50. As a result, the integrated circuit devices 40 are electrically integrated with the analyte sensor 50 upon formation of the circuitry 30, devices 40, sensor 50, and traces 55 on the substrate 20. In other words, no assembly of the integrated circuit devices 40 or sensor 50 is required after formation on the substrate 20. Therefore, a difficult manufacturing step is obviated by the embodiments described herein. Likewise, because the integrated circuit devices 40 and the analyte sensor 50 are manufactured on the same shared substrate, no additional components or mechanical connections are needed between the integrated circuit devices 40 and the analyte sensor 50.

Cross-referencing FIGS. 3 and 4, the exemplary method may include forming the electrodes 53 and conductive traces 55 by electroplating processes. After formation of the electrodes 53 and conductive traces 55, electrochemical sensing stack processing may be performed according to conventional techniques to form an electrochemical sensing stack 58 of the analyte sensor 50 with at least an analyte sensing layer (which is typically a sensor chemistry layer, meaning that materials in this layer undergo a chemical reaction to produce a signal that can be sensed by the working electrode) formed over and/or on the working electrode. The analyte sensing layer forms the sensor surface where an analyte such as glucose may bind.

It is noted that FIGS. 1-4 describe an embodiment in which the top surface 21 is processed first, with both the circuitry 30 and the integrated circuit devices 40 being formed thereon, before the bottom surface 22 is processed. However, this order of processing is not required. For example, in one embodiment, the sensor 50 may be formed over the bottom surface 22 before the integrated circuit device 40 is mounted over the top surface 21. Further as indicated above, in certain embodiments, the integrated circuit device 40 and the sensor 50, or at least portions of the sensor 50, are formed over a same surface, e.g., over the top surface 21.

Figure 5:
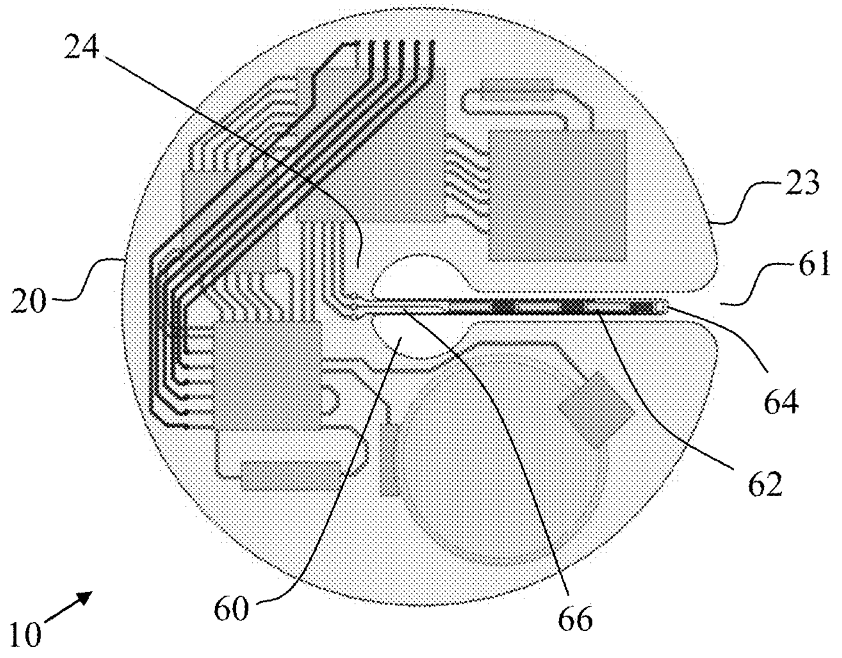
FIG. 5 is a plan view of the bottom surface of the analyte sensor device of FIG. 4 after cutting the substrate to from a voided region in accordance with an embodiment.

FIG. 5 illustrates the partially fabricated device 10 of FIG. 3 after further processing. Specifically, in FIG. 5, the substrate 20 is cut, such as by a laser cutting process, to form a voided region 60. The voided region 60 lies over the boundary between the sensor region 26 and the integrated circuit region 24 and over most of the boundary between the interconnecting region 28 and the integrated circuit region 24 (collectively shown in FIGS. 4-5) such that a prong 62 is formed with a distal end 64 and a proximal end 66. As shown, the proximal end 66 of the prong 62 remains connected to the rest of the substrate 20, i.e., to the integrated circuit region 24. The distal end 64 of the prong 62 is separated from the integrated circuit region 24 such that the prong 62 may be pivoted above the proximal end 66 to position the distal end 64 at a desired location. As shown, the voided region 60 extends to and is in communication with the peripheral edge 23 of the substrate 20. In other words, the voided region 60 includes an opening 61 or mouth at the peripheral edge 23.

Figure 6:
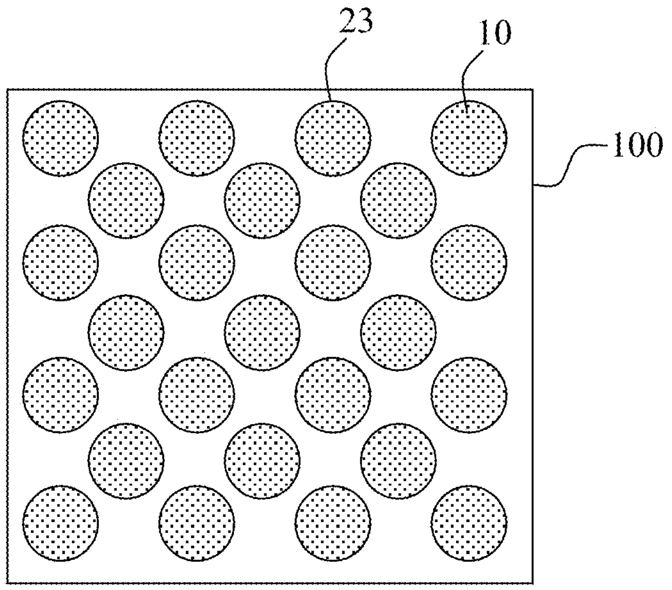
FIG. 6 is a schematic plan view of a sheet of a substrate on which a plurality of analyte sensor devices, as described in FIGS. 1-5, are located before cutting and separation in accordance with an embodiment.

For large scale manufacturing, the processing disclosed in FIGS. 1-5 may be performed on a sheet 100 of a substrate 20, as shown schematically in FIG. 6. The sheet 100 includes a plurality of partially fabricated devices 10, shown generally and without detail in FIG. 6. The cutting process described in FIG. 5 may further include cutting around the peripheral edge 23 of each partially fabricated device 10 so that each partially fabricated device 10 in FIG. 6 may be separated and removed from the sheet 100 before further processing is performed.

Figure 7:
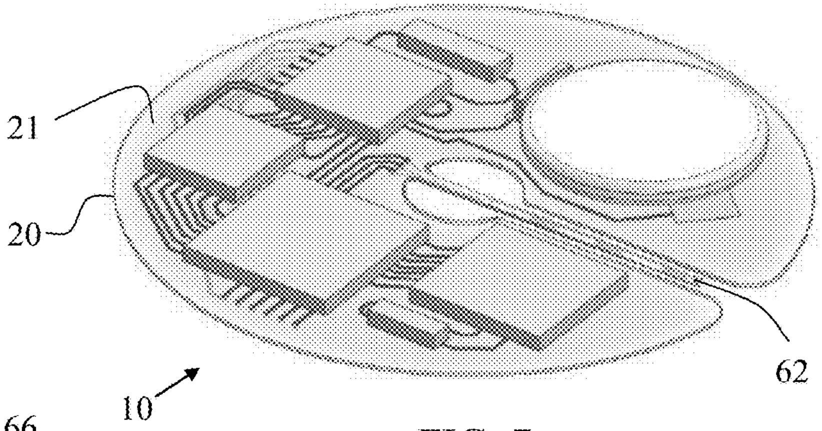
FIG. 7 is a perspective view of the analyte sensor device of FIG. 5.
Figure 8:
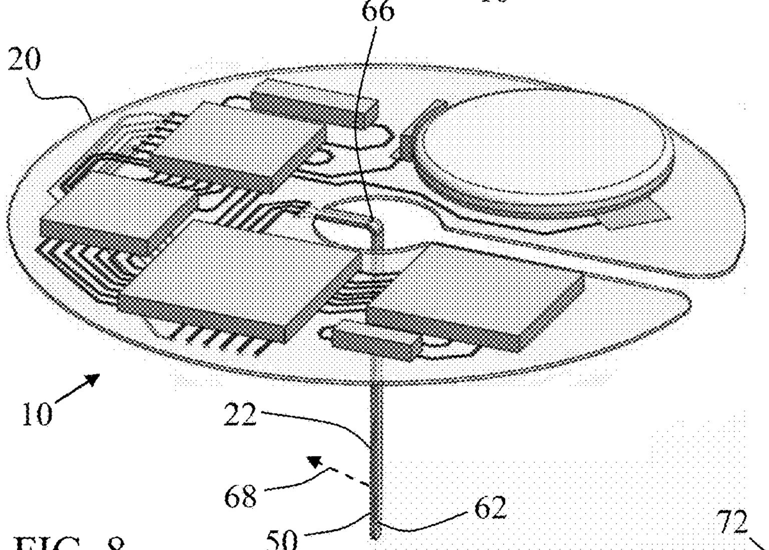
FIG. 8 is a perspective view of the analyte sensor device of FIG. 7 after bending the sensor region of the substrate in accordance with an embodiment.
Figure 9:
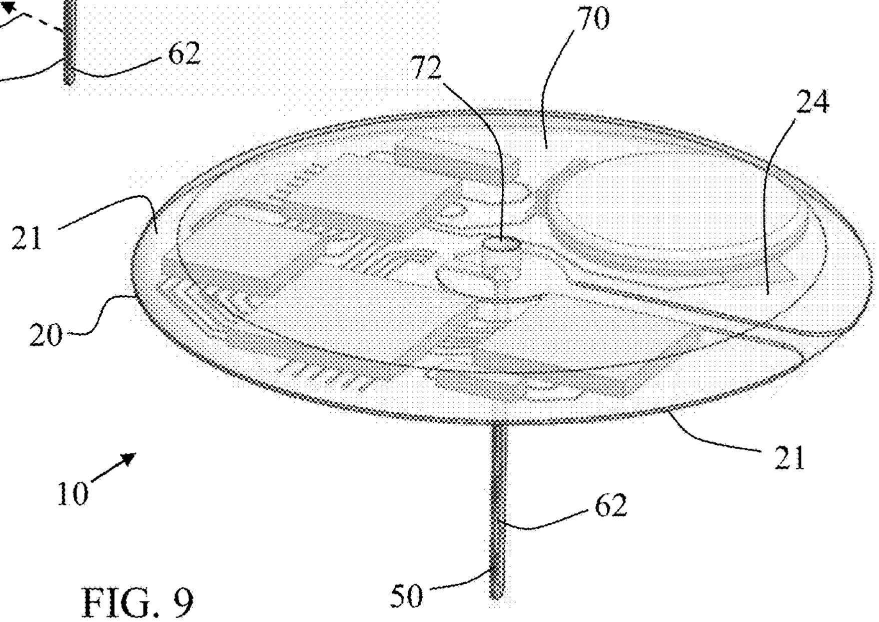
FIG. 9 is a perspective view of the analyte sensor device of FIG. 8 after forming a flexible insulative cover over the integrated circuit devices on the top surface in accordance with an embodiment.

FIG. 7 provides a perspective view of the top surface 21 of a single partially fabricated device 10 after the cutting process of FIG. 5. In FIG. 8, the prong 62, including the analyte sensor 50 is selectively bent or pivoted about the proximal end 66. In certain embodiments, the prong 62 may be bent perpendicular to the rest of the substrate 20. As shown, the bottom surface 22 of the prong 62 faces in the direction of arrow 68.

In FIG. 8, the method may continue with the formation of a flexible insulative cover 70, such as an overmold, over the top surface 21 to protect the electrical components thereon. As shown, the cover 70 may be formed with an aperture 72 located directly over, and aligned with, the prong 62. As a result, a needle may be inserted through the aperture 72 to aid with insertion of the sensor 50 into a patient's body. In an exemplary embodiment, the cover 70 may be formed from silicone, polyurethane, or other suitable material.

Further, a waterproof coating and an adhesive coating may be applied to the bottom surface 22 of the substrate 20 in the integrated circuit region 24, i.e., not on the prong 62, to facilitate adhesion to a patient's skin.

Figure 10:
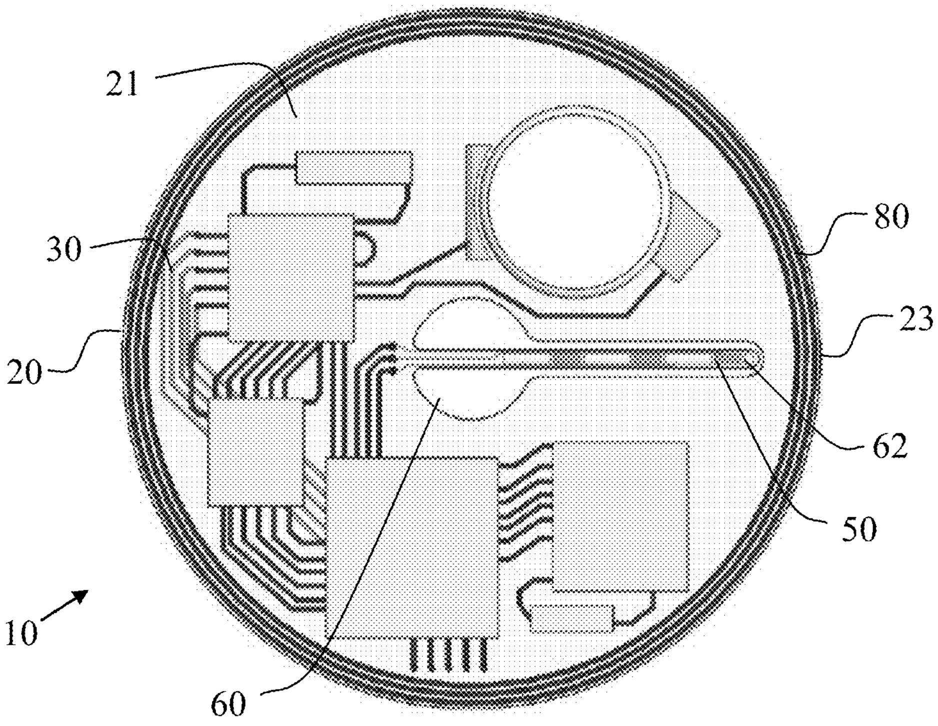
FIG. 10 is a plan view of the top surface of an alternate embodiment of the analyte sensor device, taken at the processing stage of FIG. 5 (after cutting the substrate to from a voided region).

As indicated above, FIGS. 1-9 disclose exemplary embodiments of a method for fabricating an analyte sensor device 10. FIG. 10 illustrates another embodiment of an analyte sensor device 10 that may be fabricated using similar processing. FIG. 10 is a view of the top surface 21 of the substrate 20 at the same step of processing as FIG. 5, i.e., after cutting the substrate 20 to form the voided region 60. As shown, the device 10 includes an annular antenna 80, such as a near field communications (NFC) antenna. Such an antenna 80 may be formed during the processing for forming the other circuitry 30, as described in relation to FIG. 1. As shown, the antenna 80 is electrically integrated with the circuitry 30.

Because the antenna 80 circumscribes the sensor 50, the voided region 60 in the embodiment of FIG. 10 cannot extend from the sensor 50 to the peripheral edge 23 of the substrate 20 as in the embodiment of FIG. 5. Rather, the voided region 60 is formed as a closed opening within the substrate 20. While the design of the voided region 60 and the presence of the antenna 80 distinguish the embodiment of FIG. 10 from the embodiment of FIGS. 1-9, the remaining processing may be identical to that of FIGS. 1-9, including bending the prong 62 and forming a cover over the top surface 21.

Figure 11:
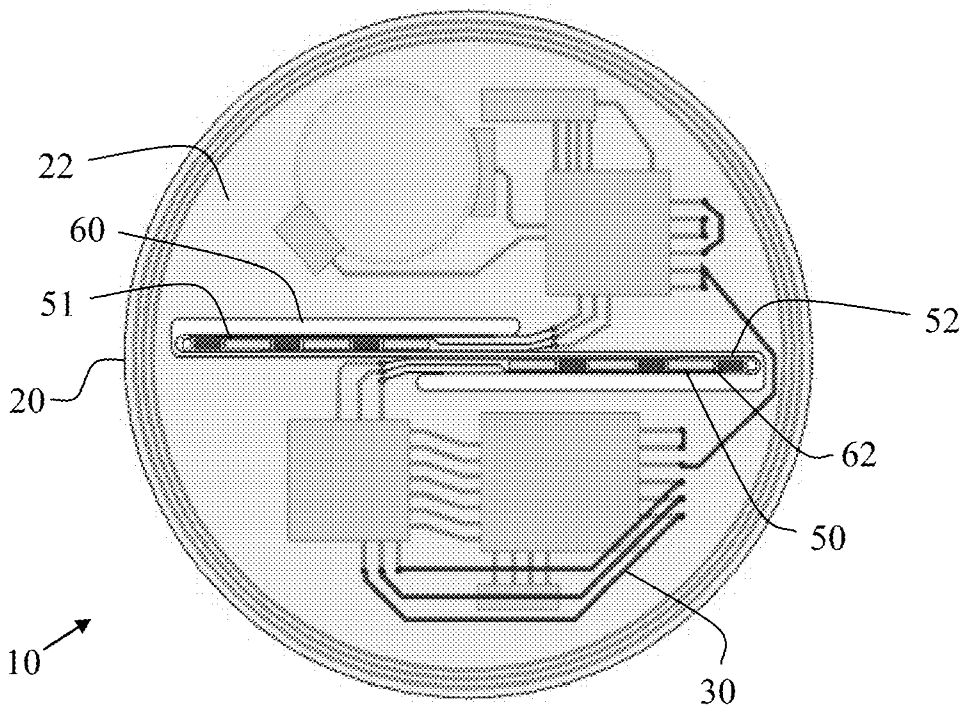
FIG. 11 is a plan view of the bottom surface of an alternate embodiment of the analyte sensor device, taken at the processing stage of FIG. 5 (after cutting the substrate to from a voided region).
Figure 12:
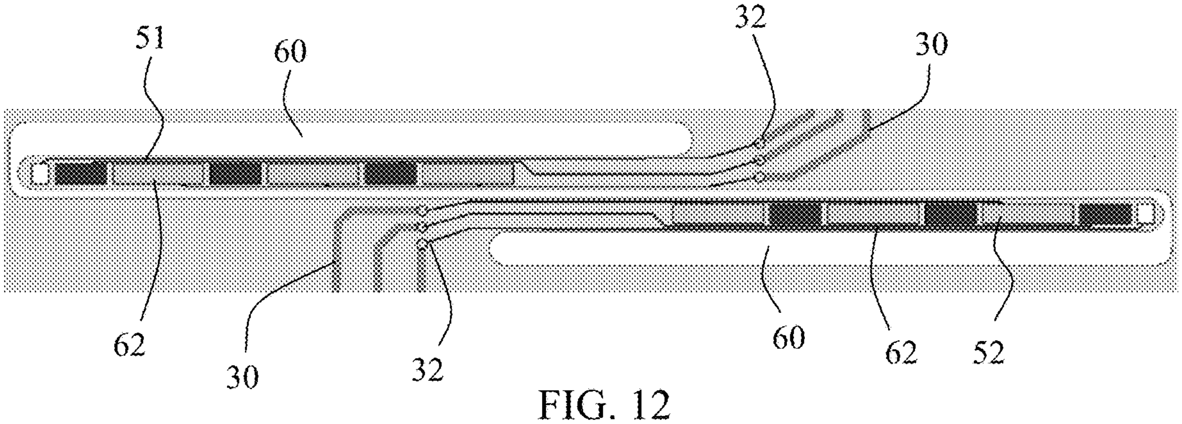
FIG. 12 is an expanded view of the voided region and sensors of the analyte sensor device of FIG. 11.
Figure 13:
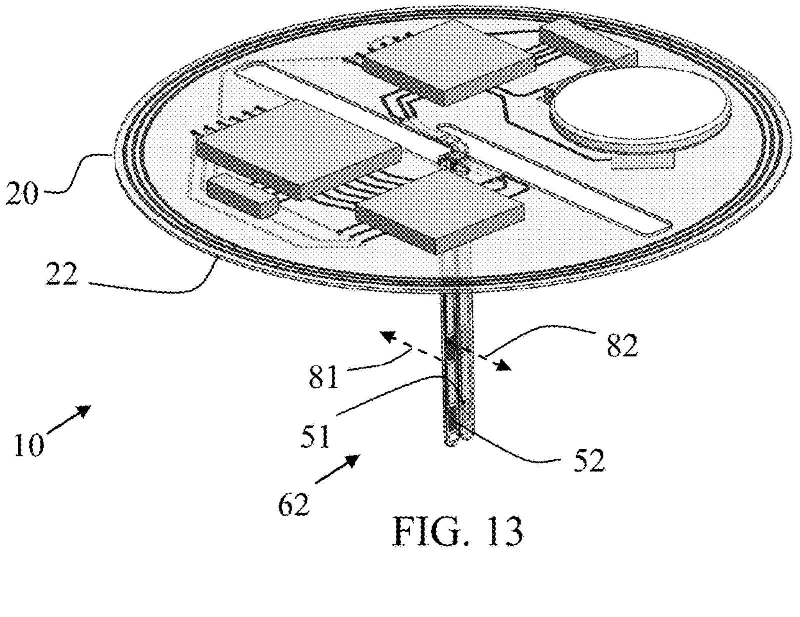
FIG. 13 is a perspective view of the analyte sensor device of FIG. 11 after bending the sensor regions of the substrate in accordance with an embodiment.

FIGS. 11-13 illustrate another embodiment of device 10. FIG. 11 is a view of the bottom surface 22 of the substrate 20. As shown in FIG. 11, the partially fabricated device 10 includes two sensors 50, a first sensor 51 and a second sensor 52. Sensors 51 and 52 are more clearly illustrated in the expanded view of FIG. 12. As shown in FIG. 12, the circuitry 30 is likewise configured for electrical connection to the sensors 51 and 52 at terminals 32. As shown, the substrate 20 is cut to form the voided region 60 to partially surround around each of the sensors 51 and 52. Further, as shown, the prongs 62 defined by the voided region 60 extend away from one another, in opposite directions.

FIG. 13 is a perspective view of the embodiment of FIGS. 11 and 12, after bending the prongs 62 on which the sensors 51 and 52 are formed. While each sensor 51 and 52 is formed over and/or in the bottom surface 22 of the substrate 20, after bending the prongs 62, the sensors 51 and 52 face opposite directions 81 and 82, respectively.

While the embodiment of FIG. 13 includes additional or different elements, processing of the embodiment of FIG. 13 may proceed similarly to the method described in FIGS. 1-9, including forming a cover over the top surface 21.

While FIGS. 1-13 have generally described a substrate 20, it is noted that the substrate 20 may include a plurality of layers and sublayers as desired. FIGS. 14-18 are schematic cross sectional views of a portion of the substrate 20 that show the processing of individual layers when performing the processes previously described in relation to FIGS. 1-4.

Figure 14:
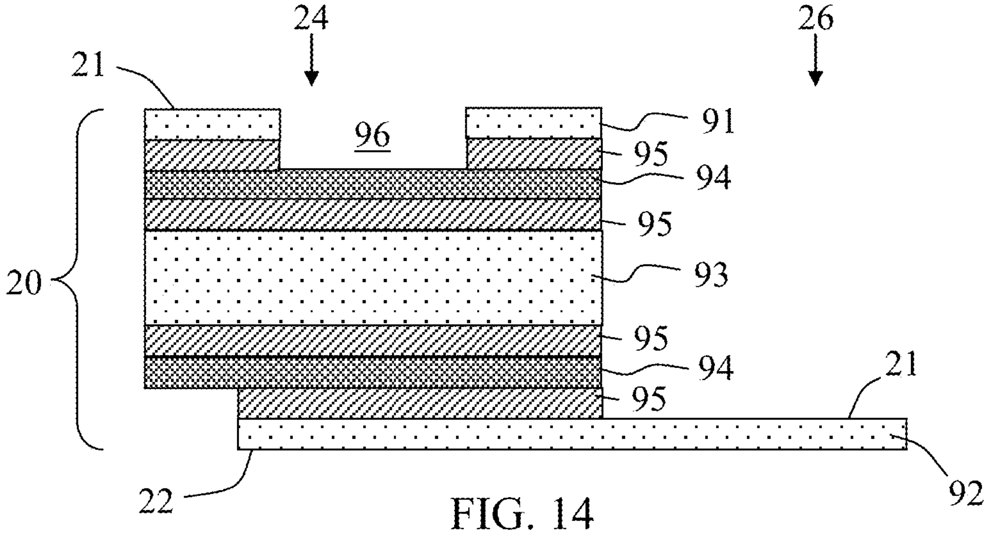
FIGS. 14-18 are schematic cross sectional views of a portion of an analyte sensor device during fabrication processing in accordance with an embodiment.

FIG. 14 corresponds to FIG. 1, in which electrical circuitry has been formed over and/or in the substrate. In FIG. 14, the substrate 20 is shown to include a top layer 91 and a bottom layer 92. In an exemplary embodiment, the top layer 91 and the bottom layer 92 are a flexible, electrically insulating material, such as polyimide, though other suitable materials may be used.

The portion of the substrate 20 that is illustrated includes the integrated circuit region 24 and the sensor region 26. The top layer 91 forms the top surface 21 of the substrate 20 in the integrated circuit region 24. Further, the bottom layer 92 forms the top surface 21 of the substrate 20 in the sensor region 26. The bottom layer 92 forms the bottom surface 22 of the substrate 20 in both the integrated circuit region 24 and the sensor region 26.

As further shown, the substrate 20 includes an intermediate layer 93 between the top layer 91 and the bottom layer 92. In an exemplary embodiment, the intermediate layer 93 is a flexible, electrically insulating material, such as polyimide, though other suitable materials may be used. Flexible conductive layers 94, such as a metallization layers, are located between the intermediate layer 93 and each of the top and bottom layers 91 and 92. The substrate 20 further includes adhesive layers 95 between each respective layer 91, 92, and 93 and the respective conductive layers 94. Exemplary conductive layers 94 are copper, platinum or another suitable metal. As is well known, each conductive layer 94 may be patterned to form a desired circuitry. Further, such patterning may provide for etching or otherwise forming vias through the intermediate layer 93 and for filling the vias with the conductive material of the conductive layers 94. Alternatively, the conductive layers 94 may be designed and formed according to the desired circuitry without patterning.

Figure 15:
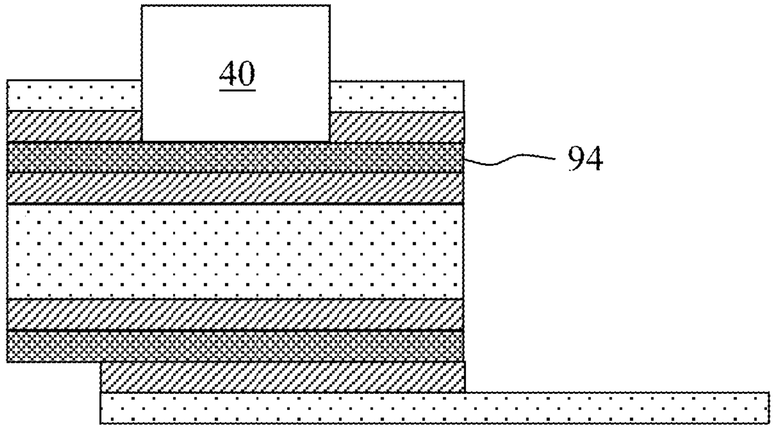

In FIG. 14, the top layer 91 and directly adjacent adhesive layer 95 are formed with a gap 96. FIG. 15 illustrates the formation of an integrated circuit device 40 in gap 96. The integrated circuit device 40 is directly electrically connected to, and integrated with, the directly underlying conductive layer 94. As noted above in relation to FIG. 2, the integrated circuit device 40 may be a microcontroller, a radio, an analog front end, a battery, or another desired electronic component, or the device 40 may be a single integrated circuit device including all necessary electronic components.

Figure 16:
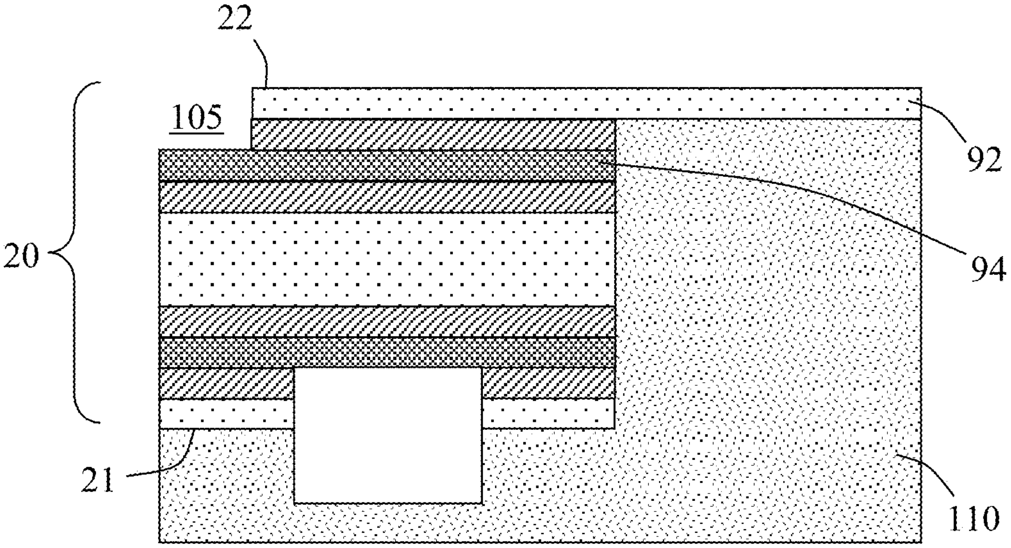
Figure 17:
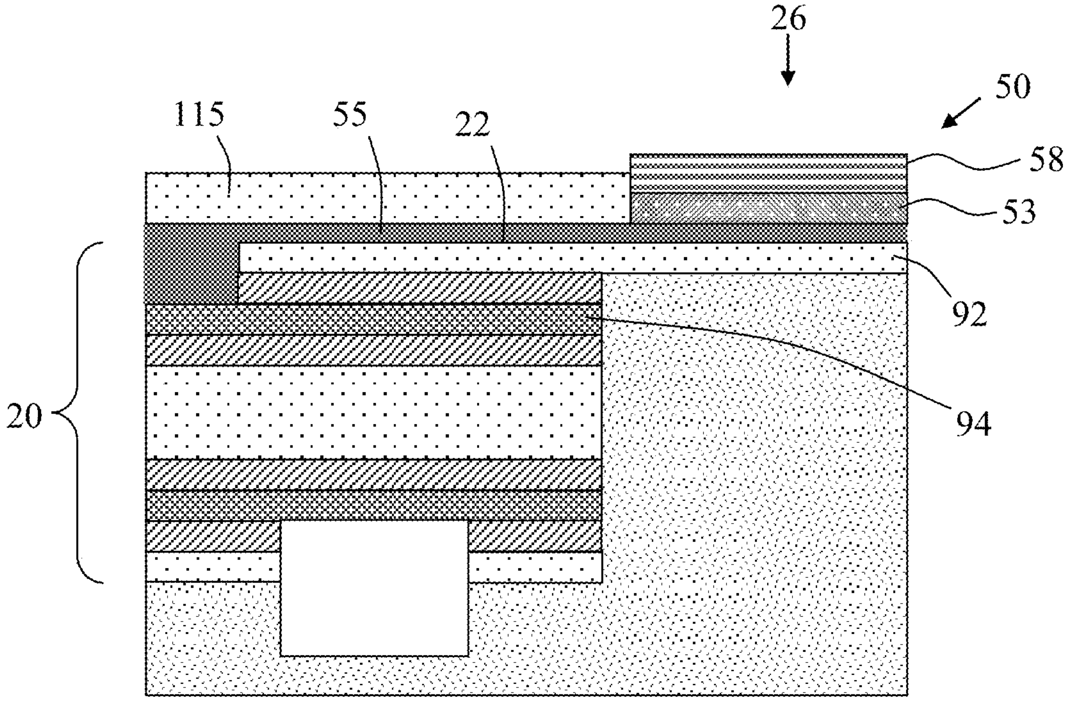

FIGS. 16 and 17 illustrate further processing for forming the analyte sensor 50. As shown, in FIGS. 16 and 17, the substrate 20 is flipped such that the bottom surface 22 faces up and the top surface 21 faces down. As shown, a gap 105 is formed adjacent the bottom layer 92 such that that underlying conductive layer 94 is exposed. Further, in FIG. 16, a mask 110 is formed over the top surface 21 of the substrate 20.

The method continues in FIG. 17 with the formation of the analyte sensor 50 over the bottom surface 22 of the substrate 20 in the sensor region 26. As shown, a conductive material is deposited in the gap 105 in contact with the conductive layer 94 and over the bottom layer 92. The conductive material forms a conductive trace 55. Further, an electrically insulating layer 115 is formed over the conductive trace 55. An exemplary insulating layer 115 is polyimide, though other suitable flexible, electrically insulating materials may be used.

As shown, the sensor 50 is then formed adjacent to the insulating layer 115 and over and in direct contact with the conductive trace 55. Specifically, the sensor electrode 53 of the sensor 50 is first formed over the bottom layer 92. An exemplary sensor electrode 53 is formed by electroplating. An exemplary sensor electrode 53 is formed from copper, platinum or another suitable metal.

Then, electrochemical sensing stack 58 may be formed over the sensor electrode 53. Electrochemical sensing stack 58 may include a plurality of layers that are not individually labeled. In an exemplary embodiment, the electrochemical sensing stack 58 includes an analyte sensing layer, such as an enzyme layer, for example a glucose oxidase layer. In an exemplary embodiment, the enzyme layer is deposited over the working electrode 53 by printing, by aerosol-based drop on demand technology, or by spin coating or spray coating. In certain embodiments, the electrochemical sensing stack 58 may include additional layers, such as a protein layer. Typically, a protein layer includes a protein such as human serum albumin, bovine serum albumin or the like. In certain embodiments, the electrochemical sensing stack 58 may include an adhesion promoter layer disposed over the analyte sensing or enzyme layer in order to facilitate contact and/or adhesion between the analyte sensing layer and another overlying layer. The adhesion promoter layer can be made from any one of a wide variety of materials known in the art to facilitate the bonding between such layers. Typically, the adhesion promoter layer includes a silane compound. In alternative embodiments, protein or like molecules in the analyte sensing layer can be sufficiently crosslinked or otherwise prepared to allow the analyte modulating membrane layer to be disposed in direct contact with the analyte sensing layer in the absence of an adhesion promoter layer. In certain embodiments, additional layers such as an interference rejection layer may be included in the electrochemical sensing stack 58. Such layers may be formed by rotary or screen printing or spin coating or spray coating or through chemical vapor deposition. In another embodiment, the adhesion promoter layer is deposited over the working electrode 53 by one of the above mentioned techniques.

The electrochemical sensing stack 58 may further include an analyte modulating layer, such as a glucose limiting membrane (GLM), over the enzyme layer. The analyte modulating layer may be provided to regulate analyte contact with the analyte sensing layer or enzyme layer. For example, the analyte modulating membrane layer can be a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable membranes known to those skilled in the art.

Figure 18:
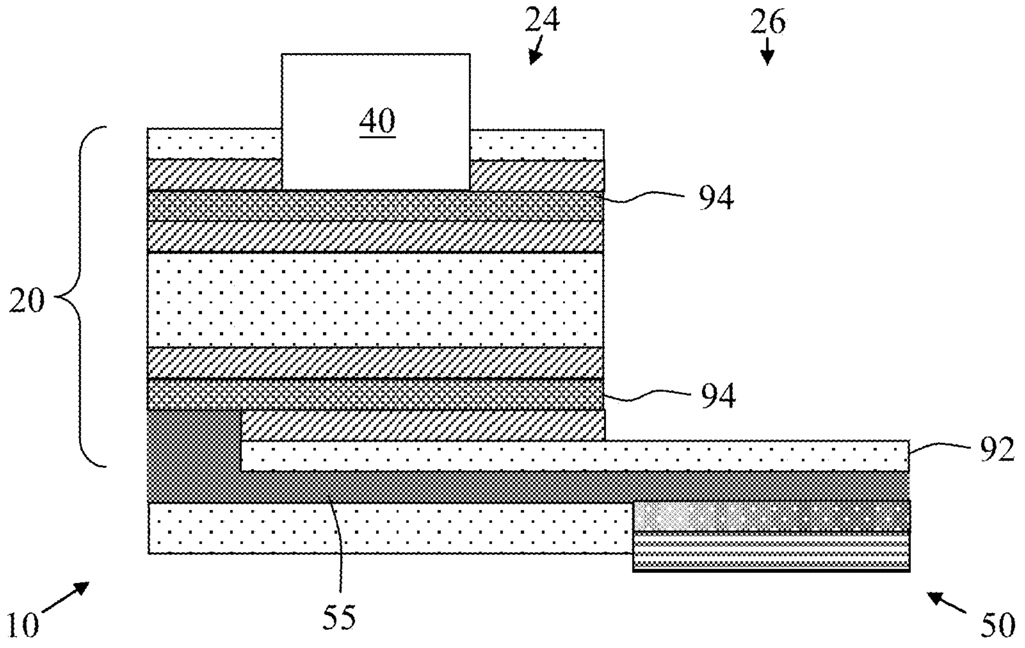

In FIG. 18, the substrate 20 is flipped over and the mask is removed. Thus, the method illustrated in FIGS. 14-18 forms a device 10 with an analyte sensor 50 in the sensor region 26. The sensor 50 is electrically connected to, and integrated with, the integrated circuit device 40 through the conductive trace 55 and the circuitry formed by the conductive layers 94 in the integrated circuit region 24. Such electrical coupling is established immediately upon formation of the sensor 50 on the bottom layer 92. In other words, the sensor 50 is not formed and then later electrically connected to the integrated circuit device 40, such as by a mechanical connection.

Figure 19:
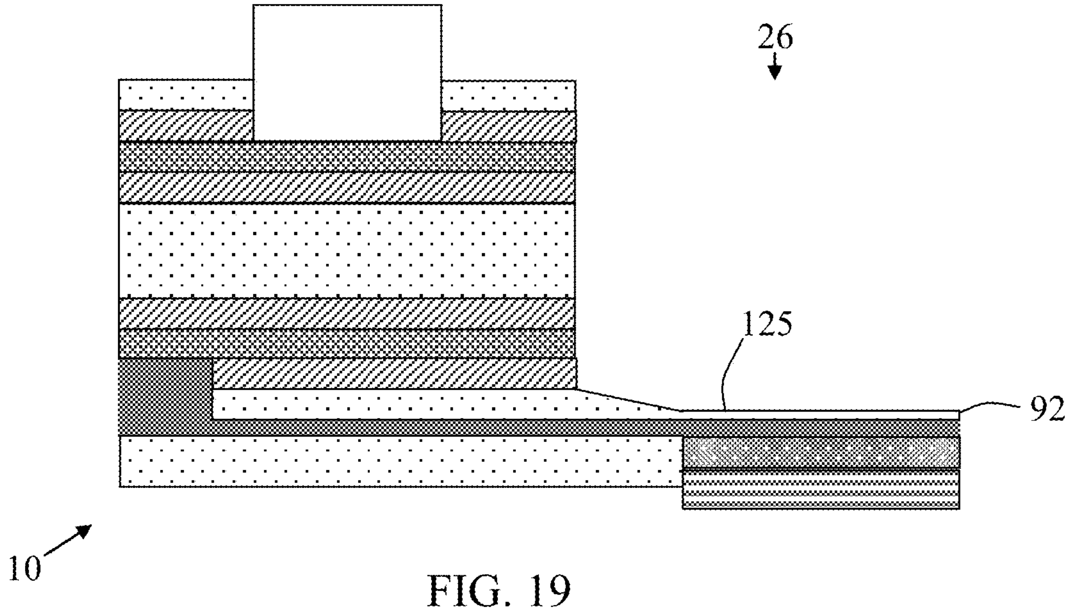
FIG. 19 is a schematic cross sectional view of a portion of an analyte sensor device in an alternate embodiment.

FIG. 19 illustrates an alternate embodiment of the device 10 of FIG. 18. In FIG. 19, the bottom layer 92 includes a thinned portion 125 in the sensor region 26. Such a structure may provide for increased flexibility, and increased comfort, when bending the sensor region 26 for insertion into a patient's body.

Figure 20:
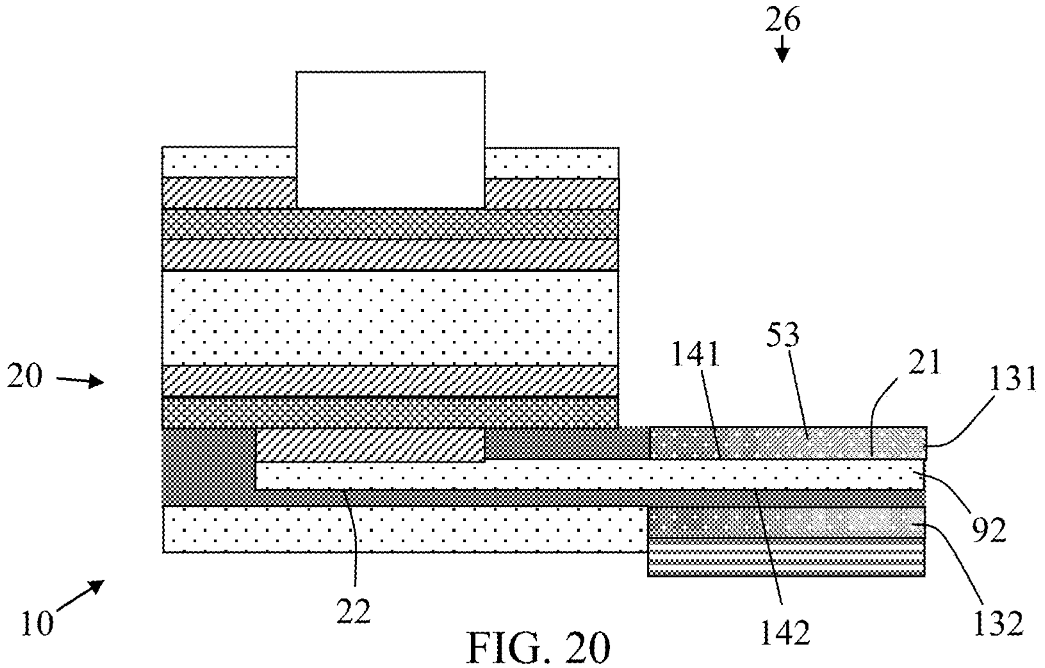
FIG. 20 is a schematic cross sectional view of a portion of an analyte sensor device in an alternate embodiment.

FIG. 20 illustrates an embodiment in which electrodes 53 are formed on both the bottom surface 22 and the top surface 21 of the substrate 20 in the sensor region 26. Specifically, a working electrode 132 is formed on the bottom surface 22 of the substrate 20, i.e., on a lower surface 142 of the bottom layer 92. Further, a counter or reference electrode 131 is formed on the top surface 21 of the substrate, i.e., on the upper surface 141 of the bottom layer 92.

Figure 21:
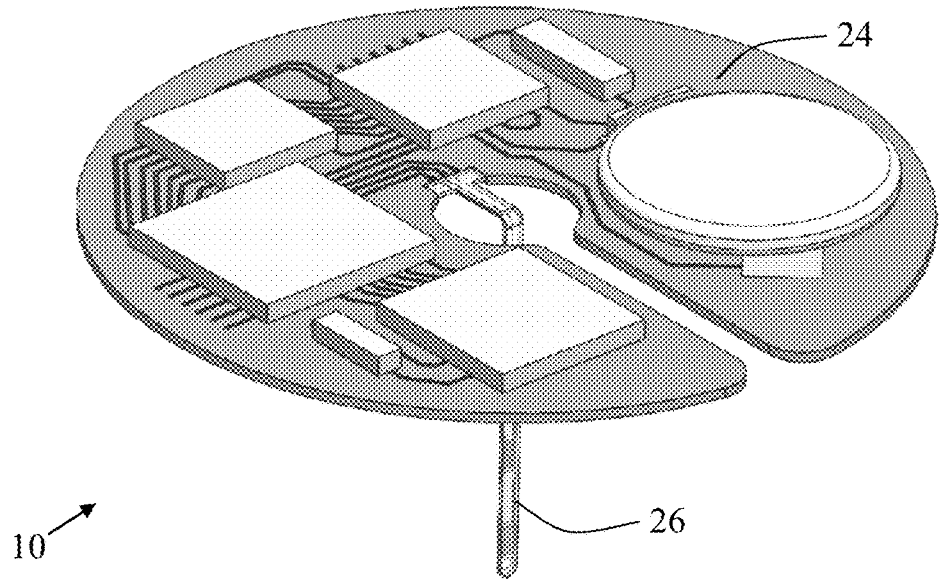
FIG. 21 is a perspective view of an alternate embodiment of an analyte sensor device taken at the processing stage of FIG. 8 (after bending the sensor region and before forming the insulative cover.
Figure 22:
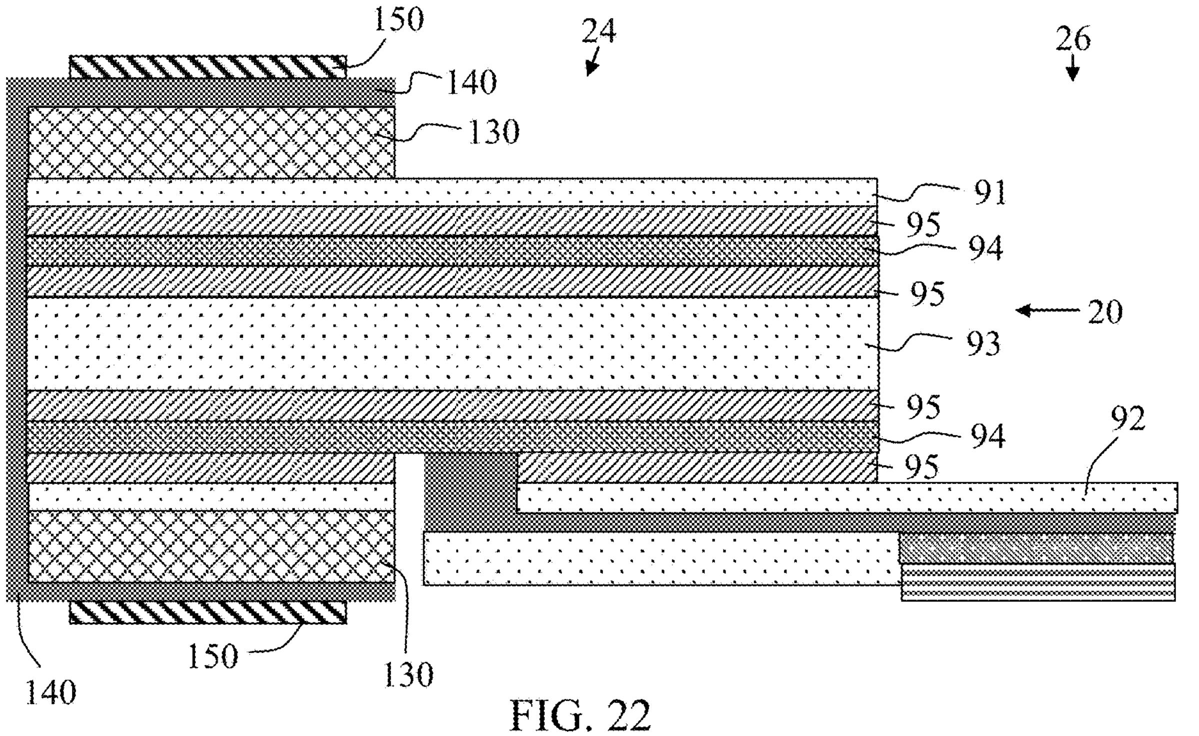
FIG. 22 is a schematic cross sectional view of a portion of the analyte sensor device of FIG. 21, taken before bending the sensor region.

FIGS. 21-22 illustrate another embodiment, in which the device 10 includes a rigid portion in the integrated circuit region 24. FIG. 21 is a perspective view of the device 10 shown after the sensor region 26 is bent to a perpendicular orientation, while FIG. 22 is a schematic cross sectional view of the connection between the integrated circuit region 24 and the sensor region 26 before the sensor region 26 is bent. Similar to the embodiment of FIG. 18, FIG. 22 illustrates that the integrated circuit region 24 includes a top layer 91, intermediate layer 93, and bottom layer 92, conductive layers 94 and adhesive layers 95. In FIG. 22, the device 10 further includes a rigid insulative layer 130 formed over the top layer 91 and over the bottom layer 92. Further, the device 10 includes a rigid conductive layer 140 over the rigid insulative layer 130. The rigid conductive layer 140 may include rigid metal, such as rigid copper. As shown, the rigid conductive layer 140 may pass vertically through the substrate 20, such as through a via hole. A coverlay may be applied over the flexible conductive layers 94. Further, a solder resist layer 150 may be applied over the rigid conductive layer 140.

Thus, the embodiment of FIGS. 21-22 provides for a rigid portion of the integrated circuit region 24 and a flexible sensor region 26 that are still electrically connected through conductive traces and circuitry formed in the flexible substrate 20. In other words, the integrated circuit region 24 and a flexible sensor region 26 are electrically integrated, and no additional mechanical coupling is needed.

Figure 23:
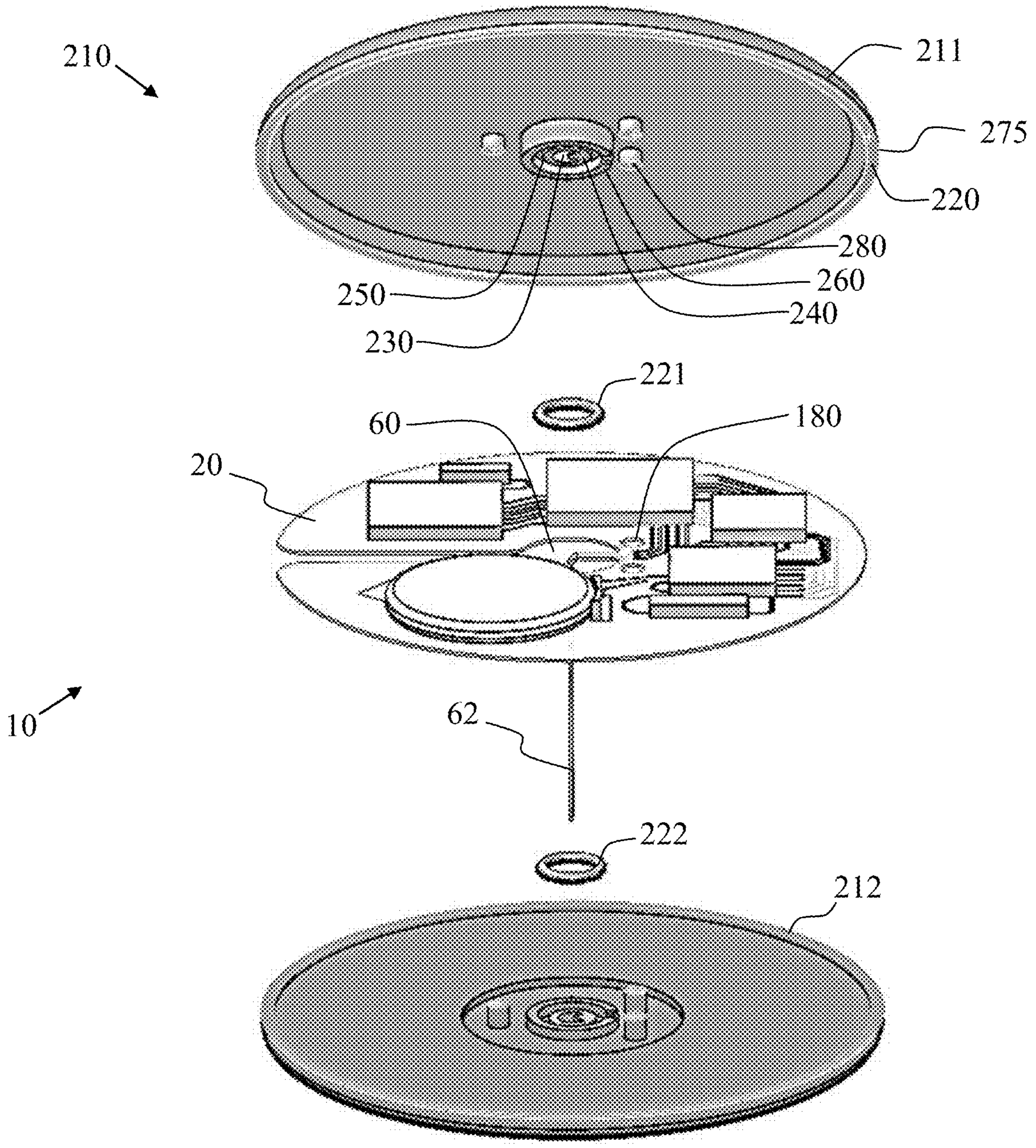
FIG. 23 is an exploded perspective view of an embodiment of an analyte sensor device with a water-tight rigid housing enclosure.
Figure 24:
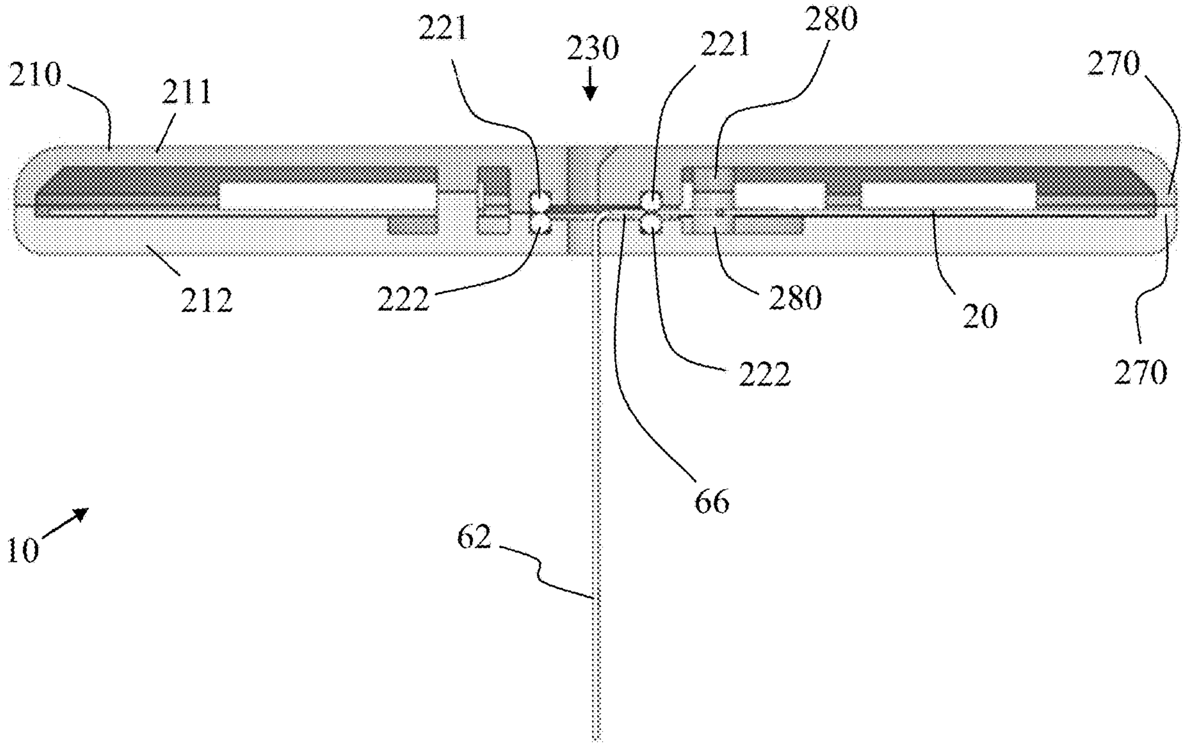
FIG. 24 is a cross sectional view of the embodiment of FIG. 23 after welding together portions of the water-tight rigid housing enclosure.

FIGS. 23-24 illustrate an embodiment in which the device 10 is provided with a rigid housing enclosure 210. The rigid housing enclosure 210 may provide a water-tight seal to waterproof the device 10.

FIG. 23 is an exploded view of the device 10, shown with an upper housing portion 211 and lower housing portion 212 surrounding the substrate 20 on which the chemical and electrical components are formed as described above. As further shown, an upper seal 221 is located between the upper housing portion 211 and the substrate 20, and a lower seal 222 is located between the lower housing portion 212 and the substrate 20. The upper and lower seals 221 and 222 may be elastically deformable. For example, the upper and lower seals 221 and 222 may be elastic O-rings 221 and 222.

As shown, each housing portion 211 and 212 includes a central aperture 230 aligned with the prong 62. As a result, a needle or cannula may be inserted through the central apertures 230 to aid with insertion of the prong 62 into a patient's body. Thus, the central aperture 230 in the upper housing portion 211 is configured to receive such a needle or cannula, while the central aperture in the lower housing portion 212 is configured to receive the needle or cannula and the prong 62. As shown, each central aperture 230 may be crescent or C-shaped such that a needle or cannula with a crescent or C-shaped cross-section may be guided through the housing 210 and around the prong 62 to facilitate insertion.

As shown, each housing portion 211 and 212 includes a central region 240 through which the aperture 230 passes. In exemplary embodiments, each central region 240 is raised, i.e., has a greater thickness than a groove or depression 250 that is formed adjacent the central portion 240. Further, each housing portion 211 and 212 may include an annular ridge 260 that is raised, i.e., has a greater thickness than the groove 250. As a result, each housing portion 211 and 212 includes a groove 250 that is partially confined by the raised features of the central region 240 and annular ridge 260.

As further shown, each housing portion 211 and 212 includes a raised outer rim 270 adjacent each respective peripheral edge 275. Further, each housing portion 211 and 212 includes raised posts 280. The posts 280 of the upper housing portion 211 are aligned with the posts 280 of the lower housing portion 212. It is noted that the substrate 20 is formed with post apertures 180 that are also aligned with the posts 280.

During assembly of the device 10 and housing 210, the O-rings 221 and 222 are positioned in the grooves 250 of the respective housing portions. In certain embodiments, the O-rings 221 and 222 may be previously fixed in the grooves 250. For example, each O-ring 221 and 222 may be co-molded in the respective grooves 250.

In either embodiment, during assembly the substrate 20 is positioned in the lower housing portion 211 over the lower O-ring 222. The substrate 20 sits within the raised outer rim 270 of the lower housing portion 211 and the posts 280 of the lower housing portion 211 may enter the post apertures 180 of the substrate 20. Thereafter, the upper housing portion 212 is positioned over the substrate 20. Again, the raised outer rim 270 of the upper housing portion 212 is radially outside of the substrate 20 such that the outer rims 270 of the housing portions 211 and 212 are directly adjacent one another. Further, the posts 280 of the upper housing portion 212 may enter the post apertures 180 of the substrate 20 and be located directly adjacent the posts 180 of the lower housing portion 211.

Referring to FIG. 24, further assembly of the housing 210 is illustrated. In FIG. 24, the upper housing portion 211 and lower housing portion 212 are sealed together, such as through ultrasonic welding or radiofrequency welding. Specifically, the surfaces of the respective outer rims 270 of the upper and lower housing portions 211 and 212 are welded together and the surfaces of the posts 280 of the upper and lower housing portions 211 and 212 are welded together. After the sealing process, the top housing portion 211 and lower housing portion 212 apply pressure on the O-rings 221 and 222. In other words, the total vertical thickness of the non-compressed O-rings 221 and 222 is less than the vertical distance between the surfaces of the grooves 250. As a result, the O-rings 221 and 222 are compressed and provide a water-tight seal where the prong 62 enters the housing 210, i.e., radially outward of the openings 230. The O-rings 221 and 222 are positioned above and below the substrate 20, which effectively "sandwich" the substrate 20. It is noted that the O-rings 221 and 222 are largely in direct contact with one another, as the O-rings 221 and 222 are aligned with the central voided region 60 of the substrate 20, and surround and sandwich the proximal end 66 of the prong 62.

It should be noted that although aspects of the above apparatuses, methods, sensors, devices, processes, etc. have been described in particular orders and in particular arrangements, such specific orders and arrangements are merely examples and claimed subject matter is not limited to the orders and arrangements as described.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A device for detecting and/or measuring one or more analytes in fluid, the device comprising:

a substrate comprising an integrated circuit region, an analyte sensor region, and an interconnecting region, wherein the analyte sensor region has a distal end, a proximal end contacting the interconnecting region, and a length dimension extending from the distal end to the proximal end, wherein the distal end and the length dimension are surrounded by a void in the substrate and are separated from the integrated circuit region by the void, wherein the void in the substrate extends along a straight direction along the substrate from the distal end to the proximal end of the analyte sensor region, wherein the proximal end is at a center axis of the substrate;

at least one analyte sensor disposed on and/or in the substrate in the analyte sensor region, wherein the at least one analyte sensor is configured to extend in the straight direction from the proximal end to the distal end along the length dimension in an unbent configuration and is configured to be bent or pivoted away from the straight direction; and an integrated circuit disposed on and/or in the substrate in the integrated circuit region, wherein the integrated circuit is electrically integrated with the at least one analyte sensor.

2. The device of claim 1 wherein the substrate has a top surface and a bottom surface opposite the top surface, wherein the integrated circuit is disposed on the top surface, and wherein the at least one analyte sensor is disposed on the bottom surface.

3. The device of claim 1 wherein the substrate has a top surface and a bottom surface opposite the top surface, wherein the integrated circuit is disposed on the top surface, and wherein the at least one analyte sensor is disposed on the bottom surface and the top surface.

4. The device of claim 1 wherein the substrate has a top surface and a bottom surface opposite the top surface, wherein at least a portion of the integrated circuit is located over the top surface, and wherein at least a portion of the at least one analyte sensor is located over the bottom surface.

5. The device of claim 1 wherein the substrate has a top surface and a bottom surface opposite the top surface, wherein the integrated circuit is disposed on the top surface, and wherein the at least one analyte sensor includes a first sensor electrode disposed on the top surface and a second sensor electrode disposed on the bottom surface.

6. The device of claim 1 wherein the substrate has a top surface and a bottom surface opposite the top surface, wherein the integrated circuit is disposed on the top surface, and wherein the at least one analyte sensor includes a first sensor electrode disposed on the top surface and on the bottom surface and wherein a second sensor electrode is disposed on the top surface and on the bottom surface.

7. The device of claim 1 wherein the analyte sensor region is formed as a prong, wherein, in a first configuration of the substrate, the prong is co-planar with the integrated circuit region of the substrate and wherein, in a second configuration of the substrate, the prong is selectively positioned at the selected angle to the integrated circuit region of the substrate.

8. The device of claim 1 wherein:

the interconnecting region of the substrate is partially surrounded by the void and contacts the integrated circuit region;

the interconnecting region is configured to be selectively bent such that the analyte sensor region of the substrate lies at a selected angle to the integrated circuit region of the substrate;

the device further comprises a conductive trace disposed on and/or in the substrate to electrically integrate the integrated circuit and the at least one analyte sensor; and the conductive trace passes through the interconnecting region.

9. The device of claim 1 wherein:

the substrate extends from a central region to the peripheral edge;

the void extends from the peripheral edge to the central region and separates a first edge of the integrated circuit region from a second edge of the integrated circuit region;

the analyte sensor region has a first edge and second edge each extending along the length dimension of the analyte sensor region;

the first edge of the analyte sensor region is spaced from the first edge of the interconnecting region by the void; and the second edge of the analyte sensor region is spaced from the second edge of the interconnecting region by the void.

10. The device of claim 9 wherein the peripheral edge forms the first edge of the integrated circuit region, the first edge of the analyte sensor region, the second edge of the analyte sensor region, and the second edge of the integrated circuit region.

11. The device of claim 1 wherein:

the substrate comprises layers of flexible material including a bottom layer, a top layer, and intermediate layers between the bottom layer and the top layer, the integrated circuit is disposed over and/or in the top layer;

the at least one analyte sensor is disposed over and/or in the bottom layer;

the bottom layer has an upper surface and a lower surface;

the at least one analyte sensor comprises a first sensor electrode disposed on and/or over the upper surface of the bottom layer and a second sensor electrode disposed on and/or over the lower surface of the bottom layer.

12. The device of claim 1 wherein:

the substrate comprises layers of flexible material including a bottom layer, a top layer, and intermediate layers between the bottom layer and the top layer;

the integrated circuit is disposed over and/or in the top layer;

the at least one analyte sensor is disposed over and/or in the bottom layer; and the intermediate layers contain conductive traces or conductive planes.

13. The device of claim 1 wherein the substrate comprises a rigid layer and a flexible layer, wherein the integrated circuit is disposed over and/or in the rigid layer, and wherein the at least one analyte sensor is disposed over and/or in the flexible layer.

14. The device of claim 1 wherein the at least one analyte sensor comprises a first analyte sensor and a second analyte sensor; wherein the substrate comprises an integrated circuit region wherein the integrated circuit is disposed, a first sensor region where the first analyte sensor is disposed, and a second sensor region where the second analyte sensor is disposed; and wherein the first sensor region and the second sensor region are selectively and independently positioned at selected angles to the integrated circuit region of the substrate such that the first analyte sensor faces a first direction and the second analyte sensor faces a second direction opposite the first direction.

15. The device of claim 1 further comprising an annular antenna disposed on and/or in the substrate and electrically integrated with the integrated circuit, the annular antenna surrounding the at least one analyte sensor and the void.

16. The device of claim 1 wherein the substrate has a disc-shaped sheet form, having a central region and the peripheral edge, and wherein the void extends from the central region toward the peripheral edge of the disc shape, and wherein the void has a greater width at the center relative to its width at the peripheral edge of the disc shape.

17. The device of claim 1 wherein the void has a linear length and a width, the linear length of the void is greater than the width of the void, and the linear length of the void extends toward the peripheral edge of the disc shape.

18. The device of claim 1 wherein the substrate comprises a sheet material and wherein the integrated circuit region, the analyte sensor region, and the interconnecting region are portions of the sheet material.

19. The device of claim 1 wherein the substrate has a first configuration, in which the integrated circuit region, the analyte sensor region, and the interconnecting region are co-planar, and a second configuration, in which the analyte sensor region is selectively positioned at a selected angle to the integrated circuit region.

20. The device of claim 1 wherein the analyte sensor region forms a prong extending at the interconnecting region from the integrated circuit region of the substrate, and wherein the distal end of the analyte sensor region is a free end of the prong that is separated from the integrated circuit region such that the prong may be pivoted relative to the integrated circuit region.

21. The device of claim 1, wherein the void in the substrate defines an edge of the substrate that extends along the entire length dimension from the distal end to the proximal end of the analyte sensor region.

22. A method for fabricating an analyte sensor device, the method comprising:

forming conductive circuitry on and/or in a substrate that has an integrated circuit region, and an analyte sensor region;

forming at least one integrated circuit device on and/or in the integrated circuit region of the substrate, wherein the at least one integrated circuit device is selectively electrically connected to the conductive circuitry;

depositing chemistry layers on and/or in the analyte sensor region of the substrate to form at least one analyte sensor integrated into the conductive circuitry, wherein the integrated circuit device and the analyte sensor form the analyte sensor device, the analyte sensor region having a distal end, a proximal end, and a length dimension extending from the distal end to the proximal end; and cutting the substrate to form a void in the substrate surrounding the distal end and extending along the length dimension from the distal end to the proximal end of the analyte sensor region, wherein the void extends along a straight direction along the substrate from the distal end to the proximal end of the analyte sensor region, wherein the void partially separates the at least one analyte sensor from the at least one integrated circuit device within the analyte sensor device, wherein the proximal end is at a center axis of the substrate wherein the at least one analyte sensor is configured to extend in the straight direction from the proximal end to the distal end along the length dimension in an unbent configuration and is configured to be bent or pivoted away from the straight direction.

23. The method of claim 22, further comprising forming an electrode on and/or in the substrate and selectively electrically connected to the conductive circuitry before forming the at least one analyte sensor, wherein the electrode electrically connects the at least one analyte sensor to the conductive circuitry.

24. The method of claim 22 wherein cutting the substrate comprises forming a prong surrounded by the void in the substrate, wherein the at least one analyte sensor is located on or in the prong, and the prong is partially separated from integrated circuit region by the void.

25. The method of claim 22 wherein:

the method further comprises selectively positioning the analyte sensor region of the substrate at a selected angle to the integrated circuit region of the substrate.

26. The method of claim 22 wherein:

the method further comprises applying an adhesive to a bottom surface of the substrate over the integrated circuit region.

27. The method of claim 22 further comprising enclosing the integrated circuit device with an overmold.

28. The method of claim 22 further comprising:

enclosing a region of the substrate including the at least one integrated circuit device in a housing enclosure; and forming a water-tight seal between the at least one analyte sensor and the enclosed region of the substrate.

29. A method for fabricating analyte sensor devices, the method comprising:

providing a sheet of a substrate;

forming conductive circuitry on and/or in the substrate in selected locations;

forming at least one integrated circuit device on and/or in an integrated circuit region of the substrate in each location, wherein each integrated circuit device is selectively electrically connected to respective circuitry therein;

depositing electrochemical sensing layers on and/or in an analyte sensor region of the substrate to form an analyte sensor in each location, wherein each analyte sensor is integrated with a respective integrated circuit device to form a respective analyte sensor device, the analyte sensor region in each location having a distal end, a proximal end, and a length dimension extending from the distal end to the proximal end;

cutting the substrate to form a void in the substrate surrounding the distal end and extending along the length dimension from the distal end to the proximal end of the analyte sensor region in each location, wherein the void partially separates the analyte sensor from the rest of the substrate at each location, wherein the void extends along a straight direction along the substrate from the distal end to the proximal end of the analyte sensor region, wherein the proximal end is at a center axis of the substrate wherein the analyte sensor is configured to extend in the straight direction from the proximal end to the distal end along the length dimension in an unbent configuration and is configured to be bent or pivoted away from the straight direction, wherein within each analyte sensor device the analyte sensor is separated from the at least one integrated circuit device; and cutting the sheet to separate each analyte sensor device.

* * * * *